United States Patent [19]
Martin

[11] Patent Number: 5,440,934
[45] Date of Patent: Aug. 15, 1995

[54] TEST APPARATUS LIMIT SWITCH ASSEMBLY

[75] Inventor: Paulo A. Martin, Fall River, Mass.

[73] Assignee: Instron Corporation, Canton, Mass.

[21] Appl. No.: 135,926

[22] Filed: Oct. 13, 1993

[51] Int. Cl.⁶ .................................................. G01B 5/30
[52] U.S. Cl. ............................................ 73/760; 73/781
[58] Field of Search ................ 73/760, 781, 811, 826, 73/816, 798, 821

[56] References Cited

U.S. PATENT DOCUMENTS

| | | | |
|---|---|---|---|
| 3,793,880 | 2/1974 | Sugi et al. | 73/811 |
| 3,994,158 | 11/1976 | Weinhold | 73/798 |
| 4,478,086 | 10/1984 | Gram | 73/781 |
| 4,691,576 | 9/1987 | Schleuniger et al. | 73/821 |

Primary Examiner—Richard E. Chilcot, Jr.
Assistant Examiner—Max H. Noori

[57] ABSTRACT

Limit switch control of crosshead materials testing machine movement in which a rod carrying slides selectively fixedly mounted thereon moves an actuator in a base, the actuator including camming surfaces and the base carrying limit switches actuatable by the camming surfaces, the actuator being slidable in the base between a neutral position to which it is biased and other positions to which the actuator is urged by the slides through the rod and slides pursuant to crosshead imposed forces.

13 Claims, 7 Drawing Sheets

TEST APPARATUS LIMIT SWITCH ASSEMBLY

FIELD

This invention relates to limit switch assemblies, useful in particular in materials testing.

BACKGROUND

It is known in the art of materials testing machines, as for testing longitudinally tensile and compressive characteristics of materials, to provide a longitudinally movable longitudinally extending rod carrying a pair of stops cooperable with a crosshead projection to be moved respectively in an extension or a compression direction, the rod cooperating with limit switches mounted in a base of such a machine to sense engagement of the projection by a stop and thereby halt crosshead movement.

SUMMARY

It has been discovered that a particularly useful materials testing apparatus and switch assembly therefor may be provided by combining a rod slidably mounted in a frame and carrying adjustably situated selectively fixed stops thereon with a crosshead projection engageable therewith and a slide actuator in the apparatus housing, a hole in the actuator being engaged by a hook on the rod, and the actuator being slidable in a base mounted in the housing, with the actuator biased in both directions toward the base and to a neutral position relative thereto, the actuator including camming surfaces cooperating with rollers to actuate a pair of limit switches so that in whichever direction the rod and actuator move there is on stop direction movement and contact first a turnoff of further movement in that direction and then a turnoff of further movement in any direction.

RELATED APPLICATIONS

This application is related to commonly-assigned applications Ser. No. 08/027,709, "TEST FRAME", filed Mar. 5, 1993, and Ser. No. 29/006,028, "MATERIALS TESTING INSTRUMENT OR THE LIKE", filed Mar. 17, 1993, the contents of which are hereby incorporated by reference herein.

PREFERRED EMBODIMENT

Description and drawings of a preferred embodiment follow.

STRUCTURE

Figure 1:
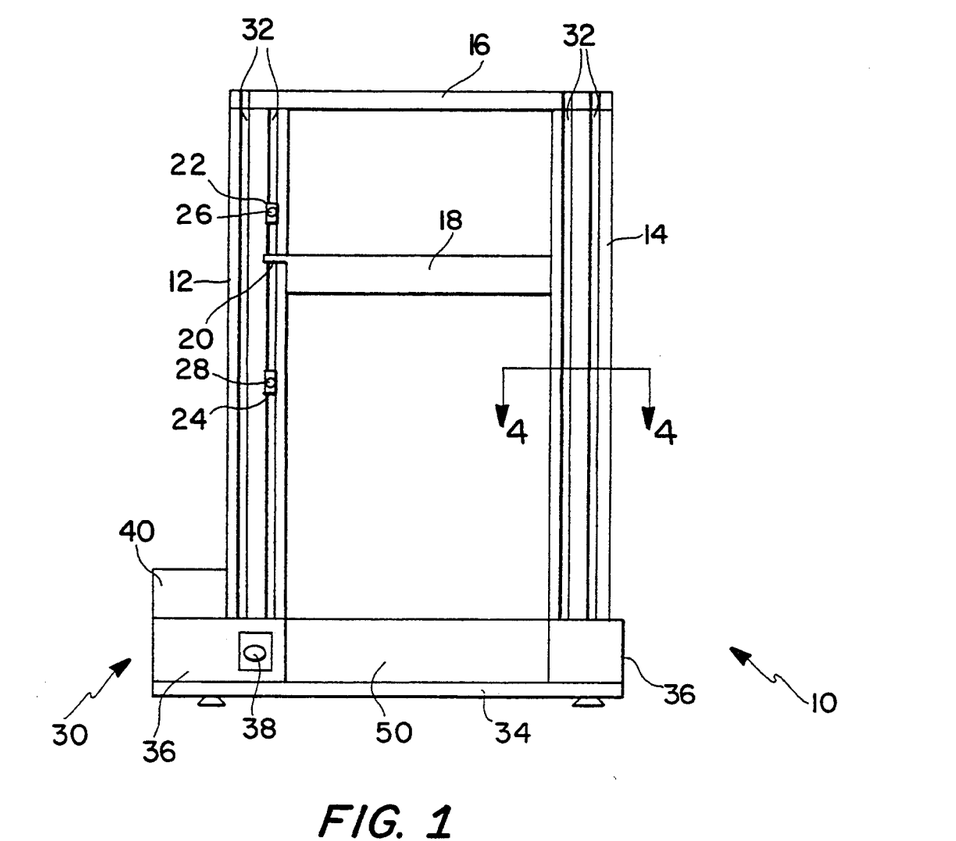
FIG. 1 is a front elevational view of a materials testing apparatus embodying the invention.

Turning now to FIG. 1, there is shown a materials testing machine frame indicated generally at 10. It includes two extruded aluminum cover columns 12, 14, a top housing 16, a crosshead 18 with protruding finger 20, movable limit stops 22, 24, with respectively cooperating knobs 26, 28, a base housing indicated generally at 30, two slots 32 in each column, cooperating with slots in top housing 16 to provide therewith three continuous slots from base housing 30 to the top of top housing 16, and a fourth along column 12.

Base housing 30 includes front lower portion 34 and front upper portion 36, integrally injection molded in single plastic molding. Extending from plastic molding 37 inset into upper portion 35 is control knob 38, and mounted on upper portion 36 are electronics components housing 40 and motor housing 42.

Interposed between coplanar surfaces 36 is a curved surface 50 defined by moving a vertical line along an arc 52 of a circle of large radius; curved surface 50 intersects a horizontal planar surface of lower portion 34 to provide a shelf.

Figure 4:
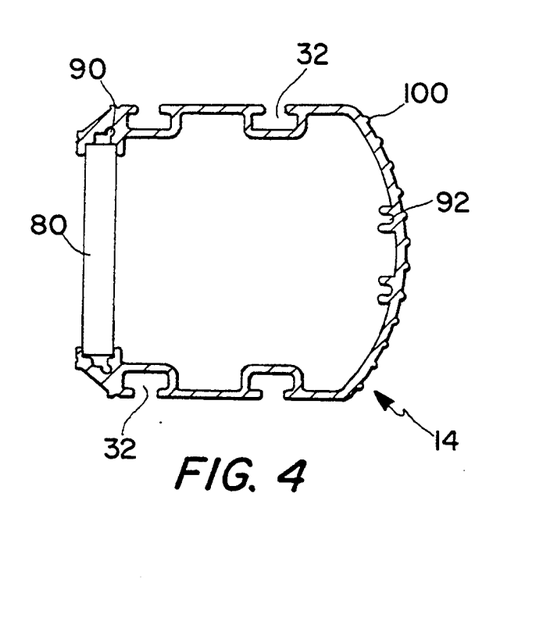
FIG. 4 is a sectional view taken at 4—4 of FIG. 1.

Column 14, a mirror image of column 12, is shown in more detail in FIG. 4.

As here seen, the slots 32 are T-shaped in cross-section.

Figure 5:
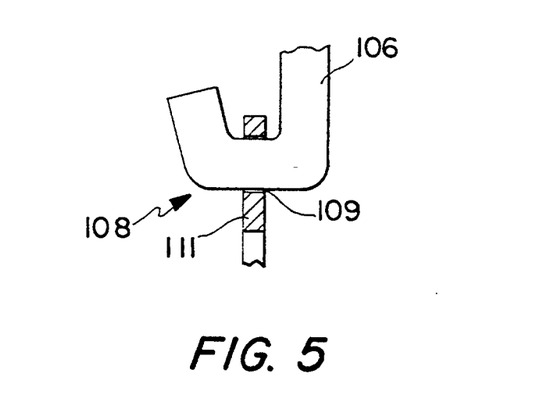
FIG. 5 is a partial View, partially in section and partially in end elevation, of the assembly of FIG. 3.

T-slides 22, 24, provided with vertical holes fixedly carrying switching rod 106 (FIGS. 5, 8) extending down to an actuator for limit switches in base 30, as will be seen, slide in column 12 and cooperate with feeler 20 carried by crosshead 18 to cause vertical movement up or down of crosshead 18 to stop as hereinafter described, as feeler 20 engages a T-slide 22, 24. The T-slides 22, 24 are selectively positionable along the length of the rod just referred,to, by loosening, moving, and retightening knobs 26, 28.

A guide rod (not shown) for crosshead 18 extends vertically from within base cover 30 to within top housing 16 within each cover 12, 14. Also extending vertically for the same extent, also within the housing 16, is a drive screw (also not shown) mounted to cooperate with crosshead 18 to drive it up and down.

As shown in FIG. 4, an accordion blind 80 is secured, by Velcro (not shown), to crosshead 18 at each end on the crosshead top, and at each end on the crosshead bottom, opposing ends being Velcro-secured (not shown) to, respectively, the bottom of top member 16 and the top of housing 30. The guide rods and drive screw are thus fully enclosed, the accordion blinds (formed of nylon cloth with a rubbery impregnant) being adapted to open and close as needed.

Figure 2:
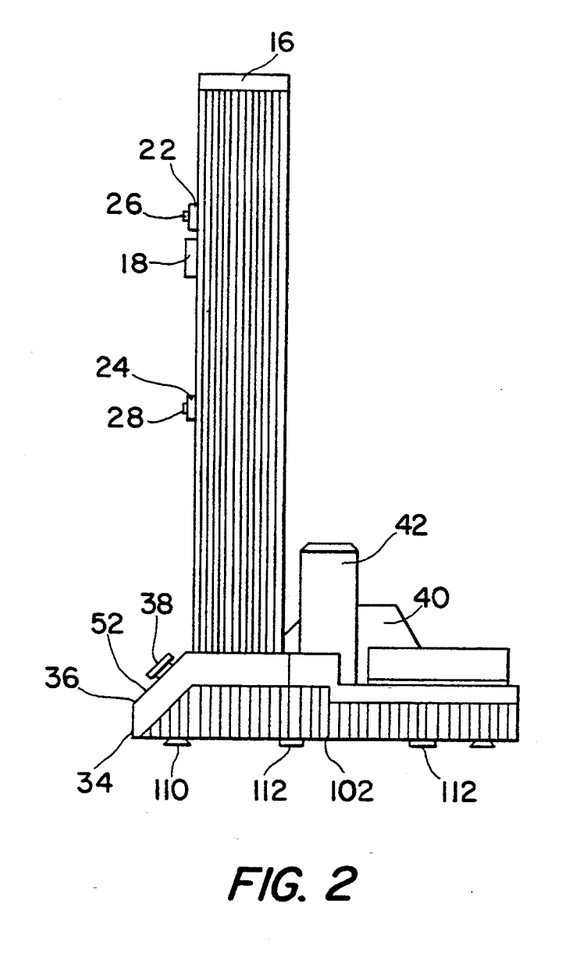
FIG. 2 is a side elevational view of said apparatus.
Figure 6:
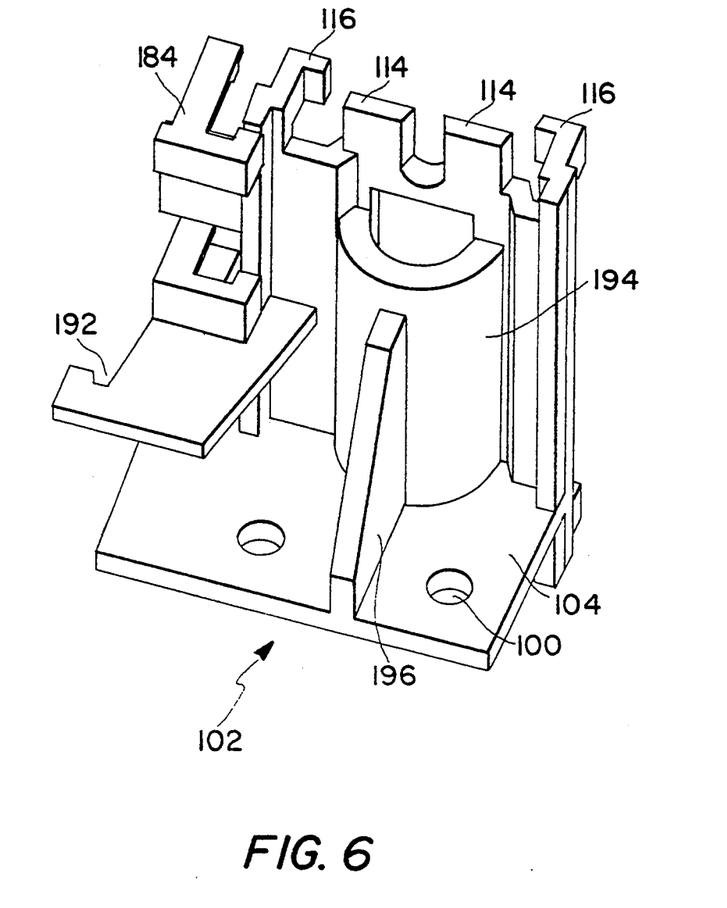
FIG. 6 is an isometric view, generally from the front part of the test apparatus, of the base element of the assembly of FIG. 3.
Figure 8:
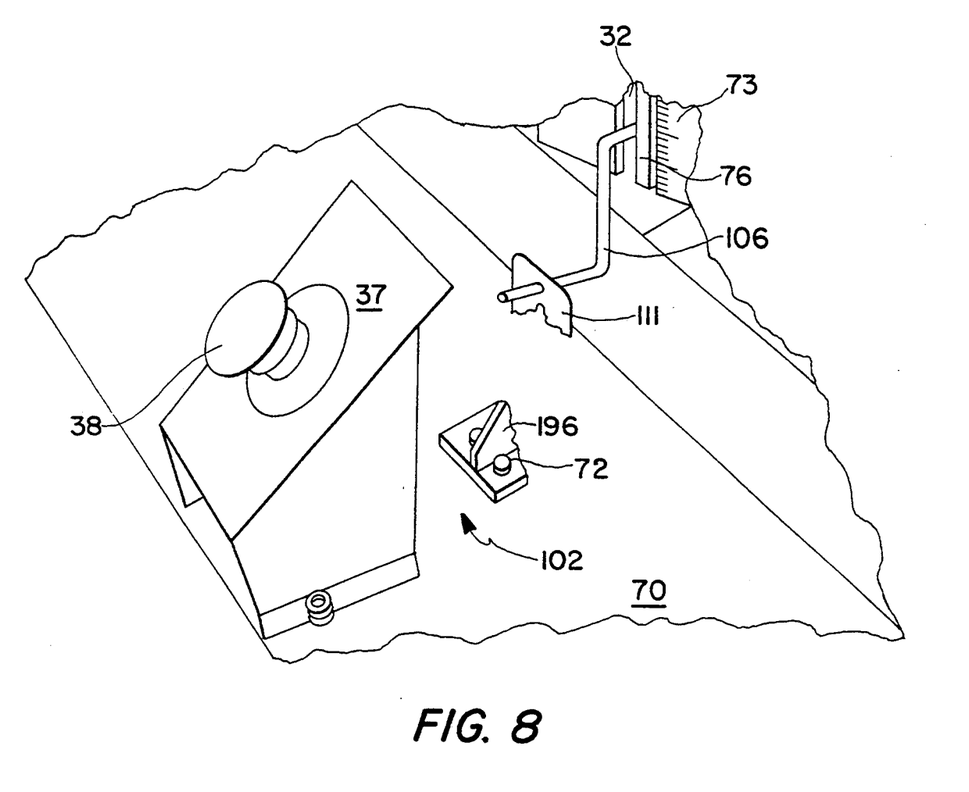
FIG. 8 is a partial isometric view, downwardly and from the right in FIG. 1, of said apparatus.

On the bottom of the embodiment are rubber feet 110 and ribs (of strong metal, U-shaped in cross-section) 112, secured on the bottom of a bottom metal plate 70 (FIG. 8) within housing 30. Also mounted on this bottom metal plate 70 with fasteners 72 extending through holes 100 (FIG. 6) is a switch base indicated generally at 102 (FIGS. 2, 6, and 8). Ledge 104, through which are holes 100, extends frontwardly of housing 30 just under inner slot 32 (FIG. 1), through which extends from above slide 22 down into housing 30 rod 106, which has as its lower end a hook indicated generally at 108.

Hook 108 extends through hole 109 of actuator slide plate 111, which is freely slidably mounted between upper pads 114 and upper L-shaped lugs 116, and lower pad 118 and lower L-shaped lugs 120. Slide plate 111 is given further support by front surfaces 122 and side lug 124, which runs in notch 126 of plate 111 and does not overlie the rear (i.e., the surface shown in FIG. 3) surface of slide plate 111.

Figure 3:
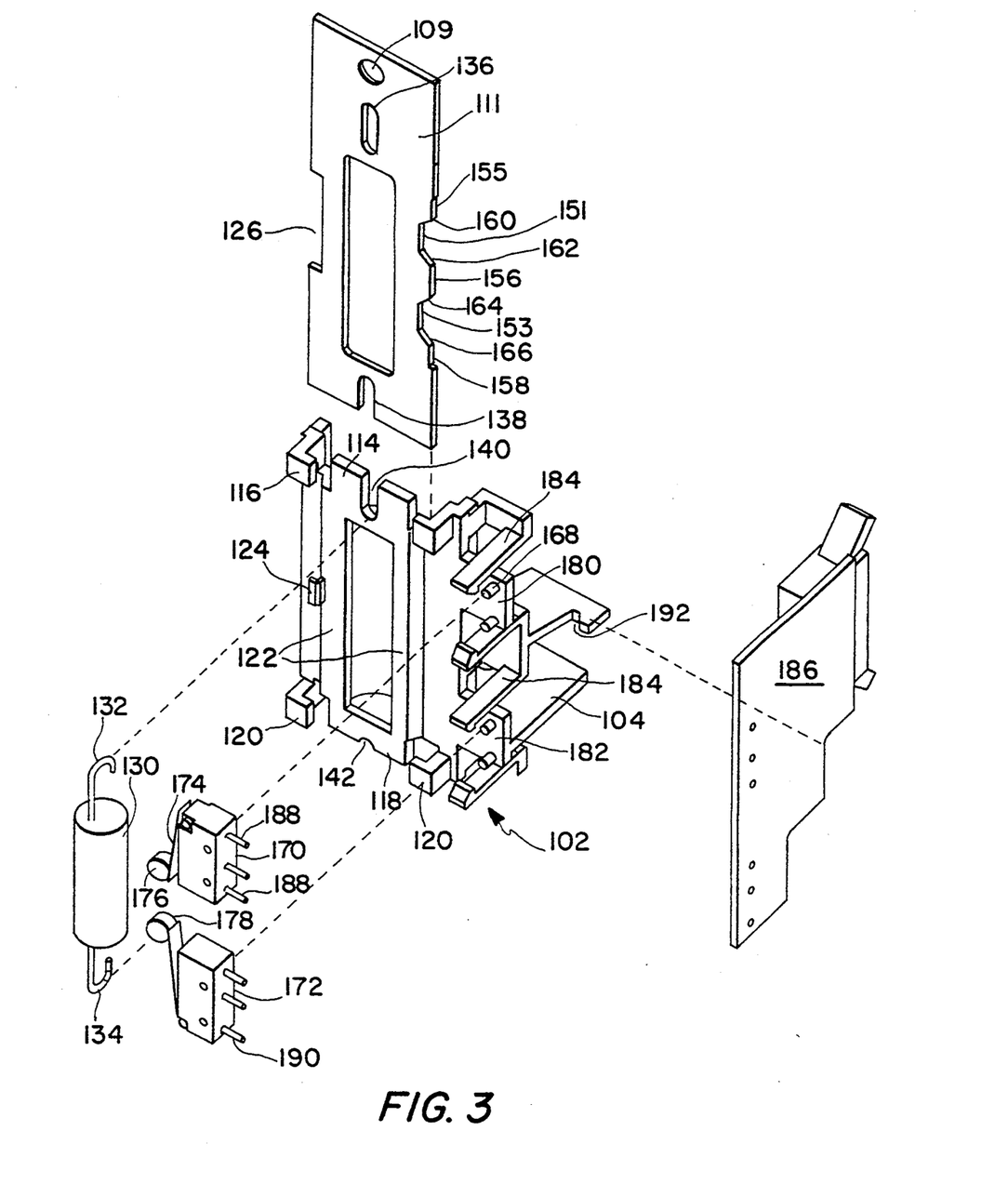
FIG. 3 is an exploded isometric view, partially diagrammatic, and generally from the rear of the apparatus, of the preferred limit switch assembly of the invention.

The upper and lower surfaces of lug 124 cooperate respectively with the upper and lower surfaces of notch 126 to provide mechanical limits respectively on downward and upward movement of plate 111, useful during assembly.

Figure 7:
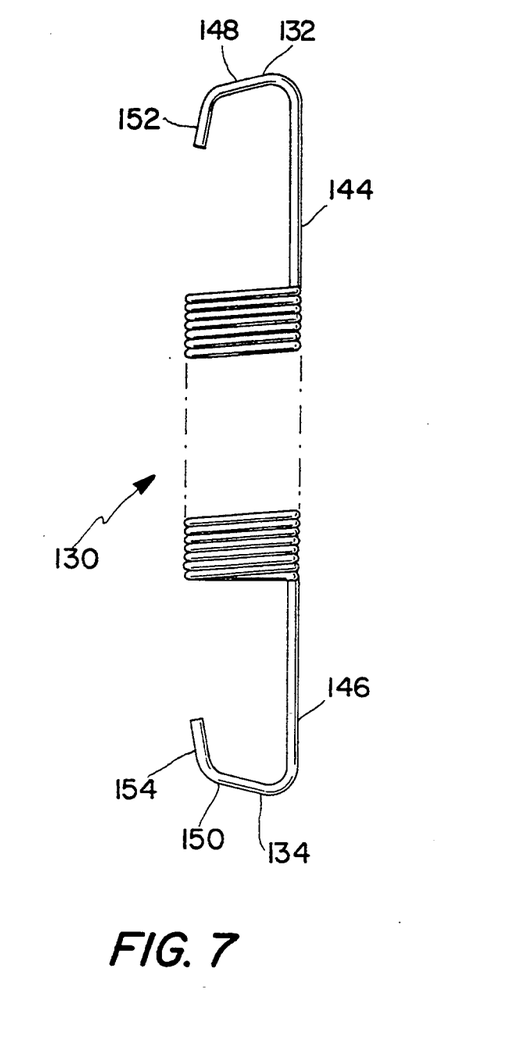
FIG. 7 is an end elevational view of an element of the assembly of FIG. 3

Spring 130, shown diagrammatically in FIG. 3, but in more detail in FIG. 7, is hooked by hooks 132 and 134 respectively in and over plate elongated hole 136 and notch 138. Spring 130 is also hooked over notches 140 and 142 in base 102 and is chosen so that when no force is imposed on slide plate 111 through rod 106 it is in a neutral position relative to base 102, a spring pretension of a little over a pound exists along the overall spring length, and some external force (greater than the weight of a rod 106 and its carried slides) is required to override the neutral position.

Spring 130, of music wire, FIG. 7, includes a pair of coaxial vertical portions 144, 146, and centrally intermediately thereof a helically wound (21.3 turns, spring rate 4.7 pounds per inch) central portion, all three portions (two vertical and one central) including outermost points having as their locus a common imaginary geometrical cylindrical surface. The vertical portions terminate into hook portions with immediately adjacent (to the vertical portions) portions 148, 150 at obtuse angles thereto of 105 degrees and outermost portions 152, 154 at 65 degrees to the immediately adjacent portions.

Actuator or slide plate 111 includes upper and lower deeper camming surfaces 151,153, upper, intermediate, and lower shallower camming surfaces 155, 156, 158, and ramping camming surfaces 160, 162 164 and 166.

Mounted on integral pegs 168 of base 102 are limit switches 170, 172, with spring steel leaf arms 174 carrying (diagrammatically only) rotatably mounted thereon rollers 176, 178, placed to roll On the appropriate camming surfaces above mentioned. The limit switches are held against surfaces 180, 182 of base 102 by arms 184 of base 102.

Printed circuit board 186 accepts pins 188, 190 of the limit switches, and the board is positioned in notch 192 of base 102.

Annular semi-cylindrical wall 194 surrounds most of spring 130 and is integral with vertical structural member 196; both are integral portions of the unitary base 102.

ASSEMBLY

The limit switch assembly shown exploded in FIG. 3 has the advantage of extremely simple and time-saving assembly.

To assemble, the lower part of slide 111 is moved under lugs 116 and over pads 114 downwardly to projection 124. The lower end of the slide is then bent rearwardly by hand until the portion of the slide below notch 126 is moved past projection 124, whereupon slide resilience snaps it back into flatness, and it is then pushed on downwardly between and below lugs 120 and surface 118.

Spring 130 is then assembled, hook 132 engaging the bottoms of hole 136 and notch 140, and hook 134 engaging the top of slot 138 and the top of notch 142. Doing this imposes on spring 130 in this position a tension of slightly over one pound, and maintains the actuator slide 111 in this neutral position in the absence of a predetermined further force imposed through hole 109 by actuator rod 106.

Limit switches 170, 172 are then placed on pegs 168, each pair of arms 184 being urged apart by the 45-degree ramping surfaces shown until the limit switches fully enter, and then snapping back to secure them in place.

PCB 186 is then assembled to pins 188, 190, and maintained there without further effort by the relationship of the parts until soldered.

As seen, assembly requires handling only six parts—the slide actuator, the base, the spring, two limit switch subassemblies, and a PCB. The base is one integral piece, injection molded of polycarbonate.

Assembly can be accomplished in under a minute, by hand without tools, following which the limit switch pins can be soldered in the PCB female terminals.

Also greatly facilitating and simplifying apparatus manufacture is the hook 108 actuating rod combination with slide 111, and the cooperation of the latter with spring 130 and the spring's hooked relation with both base and slide to provide a neutral preload maintaining initial positioning despite production variation in rod weight.

OPERATION

In operation, the actuator rod 106, which extends from slide 111 (as shown in FIGS. 3 and 8) in housing 30 up through inner slot 32 of column 12 to above slide 22, and is freely slidable in slot 32, is set for maximum desired crosshead 18 travel up and down by respectively moving slides 22 and 24 (loosening respectively through knobs 26 and 28) to the desired limit positions (and retightening there the knobs 26 and 28). (In the preferred embodiment a graduated scale 73 is provided on an elongated vertical plane surface at 45 degrees to the vertical column surfaces 76 shown in FIGS. 1 and 8 and near slot 32 for slides 22 and 24.)

When the test apparatus is actuated to move the crosshead head 18 upwardly, if tip 20 thereof engages slide 22, actuating rod 106 (on which slide 22 has been selectively non-movably secured) is moved upwardly to the same extent as is slide 22. Before crosshead tip 20 engages slide 22, roller 176 of limit switch 170 is located on cam surface 151 near the bottom thereof; upon upward movement of slide 22, and rod 106, and slide 111 With both, roller 176 rolls out and down surface 162 until just as it begins to roll onto intermediate cam surface 156 switch 170 is actuated to stop further upward movement of crosshead 18, without however interfering with then-downward movement as selected.

However, if despite the just-described action of limit switch 170 upward crosshead movement continues (a fail situation), roller 178 of limit switch 172 (which when slide 22 first engaged tip 20 was on surface 153 near the top thereof and when limit switch 170 was actuated was near the bottom of surface 153) moves on outward of and down ramp surface 166, and just as it rolls on to surface 158 actuates limit switch 172 to stop any further crosshead movement, either up or down, in a fail-safe freeze.

Conversely, downward movement of crosshead 18 whereupon tip 20 engages slide 24 causes rod 106 and slide 111 to move downwardly.

Such movement causes roller 178 of switch 172 to roll up and out surface 164, actuating limit switch 172 just as the roller 178 rolls onto surface 156, preventing (in the absence, again, of failure) further downward crosshead movement, but permitting upward crosshead movement.

Any failure-resultant further downward movement of the crosshead then causes roller 176 of limit switch 170 to roll up and out surface 160 to actuate switch 170 as the roller rolls onto surface 155, thereby preventing further crosshead movement either donor up.

The limit switches cause the actions above described through circuitry (not shown) on PCB 186, such circuitry being well understood in the art.

I claim:

1. A materials testing apparatus comprising
   a support for supporting a movable element movable with respect to said support,
   said movable element,
   linkage means movable responsive to movement of said movable element and relative to said support, and
   a switch assembly operatively connected with said linkage means, said switch assembly comprising a base,
   an actuator element carried by said base and movable with respect to said base,
   said actuator element being movable with said linkage means, and
   switching means selectively actuatable by said actuator element,
   in which said linkage means is a rod slidable with respect to said support and said rod is rectilinear in most of its length.

2. The apparatus of claim 1 in which said rod terminates in a hook and said actuator element includes a hole into which said hook fits.

3. The apparatus of claim 2 in which said actuator element is a flat plate slidably movable in said base.

4. The apparatus of claim 3 in which said actuator is slidable on a flat surface of said base.

5. The apparatus of claim 4 in which said flat surface includes opposed spring support surfaces and said actuator includes opposed spring driving surfaces, one of said support surfaces being adjacent one of said driving surfaces and the other of said support surfaces being adjacent the other of said driving surfaces.

6. The apparatus of claim 5 in which said ones are closest and said others are closest when said actuator carries to load from said linkage means large enough to move said actuator.

7. The apparatus of claim 6 which includes a spring extending between at least two of said surfaces, and in which said actuator is movable to a position in which said spring extends between only one of said support surfaces and only one of said driving surfaces.

8. The apparatus of claim 7 in which said actuator includes a camming surface and in which a limit switch is mounted on said base,
   said limit switch including a camming portion flexibly biased against said camming surface for selectively actuating said limit switch.

9. The apparatus of claim 8 in which said camming surface includes, in connected sequence, a first shallow portion, a first ramp portion, a first deep portion, a second ramp portion, a Second shallow portion, a third ramp portion, a second deep portion, a fourth ramp portion, and a third shallow portion, and said base has mounted thereon two limit switches, each including a portion flexibly biased against said camming surface, one of said limit switches having its biased portion running on said first shallow portion, said first ramp portion, said first deep portion, said second ramp portion, and said second shallow portion, and the other of said limit switches having its biased portion running on said second shallow portion, said third ramp portion, said second deep portion, said fourth ramp portion, and said third shallow portion.

10. The apparatus of claim 9 in which said base includes
    an actuator-supporting surface,
    two spaced pairs of tabs extending inwardly of said base and over said actuator for slidable movement thereof thereunder,
    a pair of limit switch support tabs,
    a pair of limit switch holding arms extending from each limit switch support tab and latchably biased each toward a respective limit switch,
    a notched printed circuit board abutment plate, and
    a mounting shelf.

11. The apparatus of claim 10 in which
    said spring includes an intermediate helically wound portion terminating in opposed coaxial rectilinear portions, said helically wound portion and said rectilinear portions having outer points lying in a common cylindrical surface.

12. The apparatus of claim 11 in which said base includes a curved shield around at least a portion of said spring.

13. The apparatus of claim 12 in which said base is integrally injection molded of plastic.

* * * * *